US011471085B2

(12) United States Patent
Mrvaljevic et al.

(10) Patent No.: US 11,471,085 B2
(45) Date of Patent: Oct. 18, 2022

(54) ALGORITHMS FOR DETECTING ATHLETIC FATIGUE, AND ASSOCIATED METHODS

(71) Applicant: Strive Tech Inc., Lynwood, WA (US)

(72) Inventors: Nikola Mrvaljevic, Bothell, WA (US); Filipp Shpomer, Redmond, WA (US); Carsten Gabriel Winsnes, Seattle, WA (US)

(73) Assignee: STRIVE TECH INC., Lynnwood, WA (US)

( * ) Notice: Subject to any disclaimer, the term of this patent is extended or adjusted under 35 U.S.C. 154(b) by 180 days.

(21) Appl. No.: 16/316,596

(22) PCT Filed: Jul. 11, 2017

(86) PCT No.: PCT/US2017/041553
§ 371 (c)(1),
(2) Date: Jan. 9, 2019

(87) PCT Pub. No.: WO2018/013580
PCT Pub. Date: Jan. 18, 2018

(65) Prior Publication Data
US 2019/0290181 A1    Sep. 26, 2019

Related U.S. Application Data

(60) Provisional application No. 62/360,952, filed on Jul. 11, 2016.

(51) Int. Cl.
*A61B 5/00*    (2006.01)
*A61B 5/22*    (2006.01)
(Continued)

(52) U.S. Cl.
CPC ............... *A61B 5/224* (2013.01); *A61B 5/00* (2013.01); *A61B 5/02* (2013.01); *A61B 5/0205* (2013.01);
(Continued)

(58) Field of Classification Search
CPC .. A61B 5/224; A61B 5/24; A61B 5/00; A61B 5/02; A61B 5/0205; A61B 5/02438;
(Continued)

(56) References Cited

U.S. PATENT DOCUMENTS 5,163,440 A * 11/1992 DeLuca ................. G16H 40/63
                                                                600/587
5,318,039 A * 6/1994 Kadefors ............... A61B 5/389
                                                                600/587

(Continued)

FOREIGN PATENT DOCUMENTS

CN    103445777 A  * 12/2013
CN    103445777 B    12/2013
(Continued)

OTHER PUBLICATIONS

International Preliminary Report on Patentability dated Jan. 24, 2019, issued in corresponding Application No. PCT/US2017/041553, filed Jul. 11, 2017, 11 pages.
(Continued)

*Primary Examiner* — Carl H Layno
*Assistant Examiner* — Michael J Lau
(74) *Attorney, Agent, or Firm* — Christensen O'Connor Johnson Kindness PLLC

(57) ABSTRACT

Systems and methods for detecting athletic performance and fatigue are disclosed herein. In one embodiment, a method for monitoring athletic performance of an athlete includes: monitoring a heart rate (HR) of the athlete by a wearable electrocardiogram (ECG) sensor carried by the athlete; determining a rate of change of the HR over a period of time; comparing the rate of change to a predetermined threshold; and based on the comparing, determining whether the athlete is fatigued.

20 Claims, 13 Drawing Sheets

(51) Int. Cl.

| | |
|---|---|
| *G16H 20/30* | (2018.01) |
| *A61B 5/0205* | (2006.01) |
| *A61B 5/02* | (2006.01) |
| *A61B 5/103* | (2006.01) |
| *A61B 5/024* | (2006.01) |
| *A61B 5/11* | (2006.01) |
| *A61B 5/24* | (2021.01) |
| *A41B 1/00* | (2006.01) |
| *A41D 1/08* | (2018.01) |
| *A61B 5/0245* | (2006.01) |
| *A61B 5/332* | (2021.01) |
| *A61B 5/389* | (2021.01) |

(52) U.S. Cl.
CPC .......... *A61B 5/02438* (2013.01); *A61B 5/103* (2013.01); *A61B 5/11* (2013.01); *A61B 5/24* (2021.01); *A61B 5/6804* (2013.01); *G16H 20/30* (2018.01); *A41B 1/00* (2013.01); *A41D 1/08* (2013.01); *A61B 5/0245* (2013.01); *A61B 5/02405* (2013.01); *A61B 5/1116* (2013.01); *A61B 5/1118* (2013.01); *A61B 5/332* (2021.01); *A61B 5/389* (2021.01); *A61B 2503/10* (2013.01); *A61B 2562/0219* (2013.01)

(58) Field of Classification Search
CPC ......... A61B 5/103; A61B 5/11; A61B 5/6804; A61B 5/389; A61B 5/332; A61B 5/02405; A61B 5/1116; A61B 5/1118; A61B 2562/0219; G16H 20/30; A41B 1/00; A41D 1/08
USPC ...................................................... 600/301
See application file for complete search history.

(56) References Cited

U.S. PATENT DOCUMENTS

| | | | | |
|---|---|---|---|---|
| 5,349,963 A * | 9/1994 | Eskelinen | A61B 5/389 | 600/546 |
| 6,015,388 A * | 1/2000 | Sackner | A61M 16/00 | 600/534 |
| 6,238,338 B1 * | 5/2001 | DeLuca | A61B 5/681 | 128/903 |
| 9,131,888 B2 * | 9/2015 | Grey | A61B 5/7275 | |
| 2001/0049482 A1 * | 12/2001 | Pozos | A61B 5/225 | 600/587 |
| 2005/0113703 A1 * | 5/2005 | Farringdon | A61B 5/25 | 600/509 |
| 2005/0177059 A1 * | 8/2005 | Koivumaa | A61B 5/389 | 600/546 |
| 2005/0283205 A1 * | 12/2005 | Lee | A61B 5/389 | 607/48 |
| 2006/0079800 A1 * | 4/2006 | Martikka | A61B 5/222 | 600/546 |
| 2007/0219059 A1 * | 9/2007 | Schwartz | A61B 5/02405 | 482/8 |
| 2008/0161654 A1 * | 7/2008 | Teller | A61B 5/4884 | 600/300 |
| 2009/0023554 A1 * | 1/2009 | Shim | A63B 22/02 | 482/4 |
| 2010/0113898 A1 * | 5/2010 | Kim | A61B 5/318 | 600/310 |
| 2010/0179438 A1 * | 7/2010 | Heneghan | A61B 5/0002 | 600/595 |
| 2010/0292606 A1 * | 11/2010 | Prakash | A61B 5/4023 | 600/554 |
| 2011/0065504 A1 * | 3/2011 | Dugan | A63F 13/42 | 463/31 |
| 2011/0105861 A1 * | 5/2011 | Derchak | G16H 20/30 | 600/301 |
| 2011/0130643 A1 * | 6/2011 | Derchak | A63B 24/0006 | 600/534 |
| 2012/0071732 A1 * | 3/2012 | Grey | A61B 5/112 | 600/549 |
| 2012/0071733 A1 * | 3/2012 | Grey | A61B 5/0006 | 600/301 |
| 2012/0253484 A1 * | 10/2012 | Burich | G16H 40/67 | 700/91 |
| 2013/0012790 A1 * | 1/2013 | Horseman | A61B 5/6891 | 600/301 |
| 2013/0171599 A1 * | 7/2013 | Bleich | G16H 20/30 | 434/247 |
| 2014/0206948 A1 * | 7/2014 | Romem | A61B 5/6805 | 600/301 |
| 2015/0005608 A1 * | 1/2015 | Evans | A61B 5/30 | 600/382 |
| 2015/0005911 A1 * | 1/2015 | Lake, II | A63B 71/06 | 700/91 |
| 2015/0019135 A1 * | 1/2015 | Kacyvenski | G09B 19/00 | 702/19 |
| 2015/0038806 A1 * | 2/2015 | Kaleal, III | A61B 5/4833 | 600/301 |
| 2015/0051471 A1 * | 2/2015 | Clare | A61B 5/1107 | 600/391 |
| 2015/0182113 A1 * | 7/2015 | Utter, II | A61B 5/721 | 340/539.12 |
| 2015/0351690 A1 * | 12/2015 | Toth | A61B 5/6839 | 600/391 |
| 2016/0106365 A1 * | 4/2016 | Choi | A61B 5/742 | 600/301 |
| 2016/0128626 A1 * | 5/2016 | Johnson | G16H 20/40 | 600/300 |
| 2016/0143579 A1 * | 5/2016 | Martikka | A61B 5/0205 | 600/301 |
| 2016/0166152 A1 * | 6/2016 | Jaatinen | A61B 5/0205 | 600/483 |
| 2016/0180059 A1 * | 6/2016 | Kuo | G06V 40/23 | 434/247 |
| 2016/0183818 A1 * | 6/2016 | Richards | A61B 5/02433 | 600/479 |

FOREIGN PATENT DOCUMENTS

| | | | | |
|---|---|---|---|---|
| WO | 2012063982 A1 | 5/2012 | | |
| WO | WO-2012063982 A1 * | 5/2012 | ......... | G06Q 30/0255 |
| WO | 2015160272 A1 | 10/2015 | | |
| WO | WO-2015160272 A1 * | 10/2015 | .......... | A61B 5/0507 |

OTHER PUBLICATIONS

International Search Report and Written Opinion dated Nov. 9, 2017, issued in corresponding application No. PCT/US2017/041553, filed Jul. 11, 2017, 14 pages.

* cited by examiner

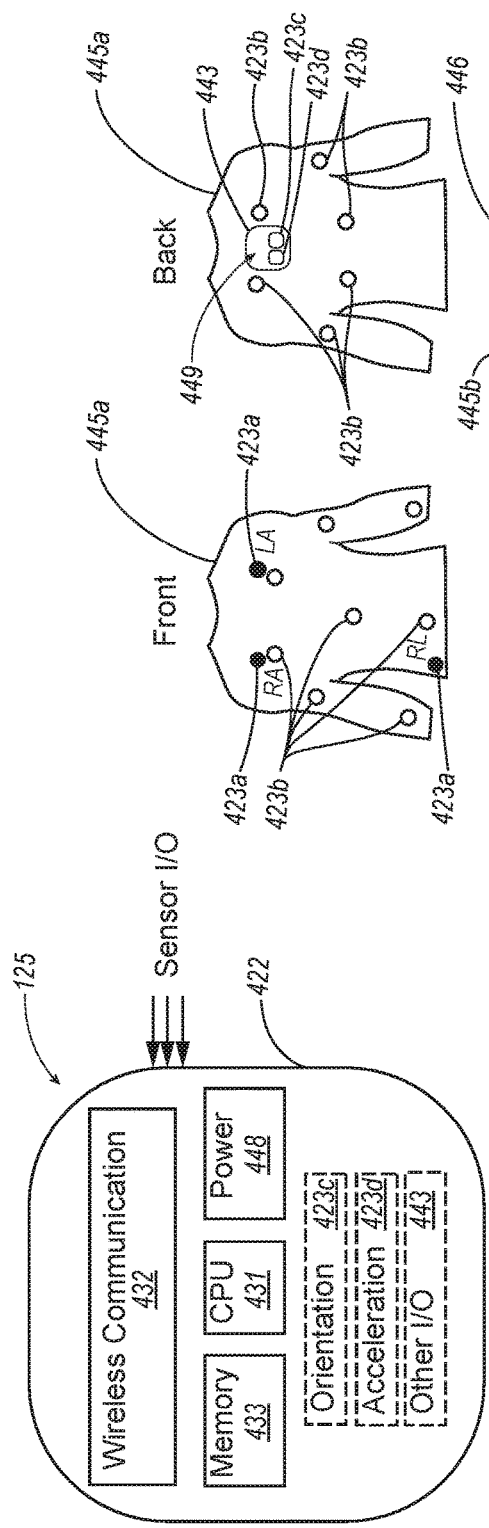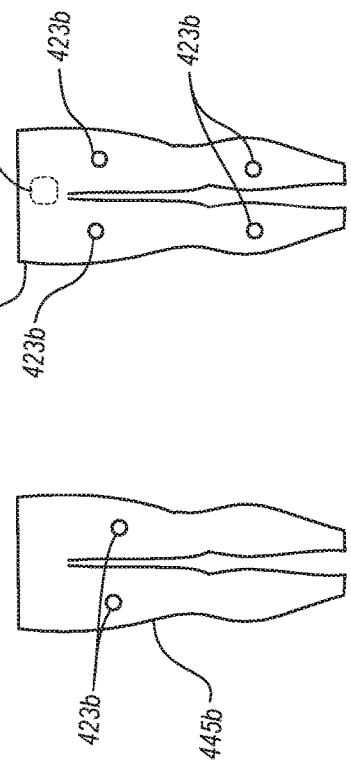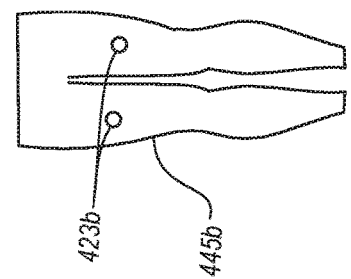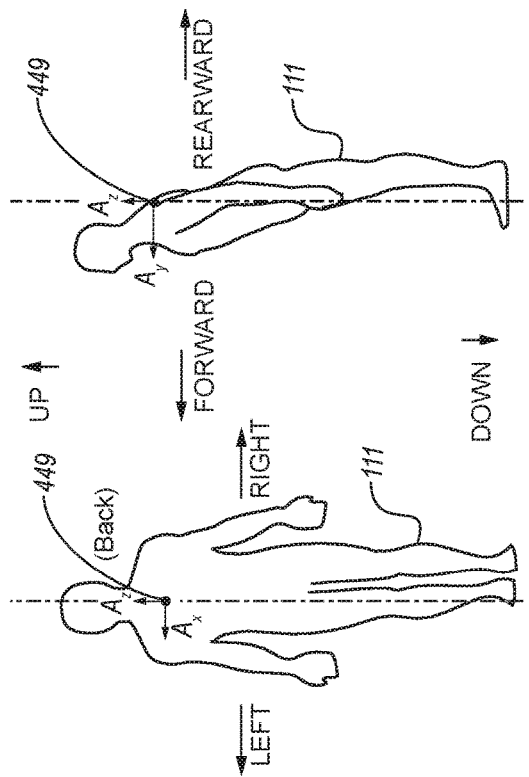

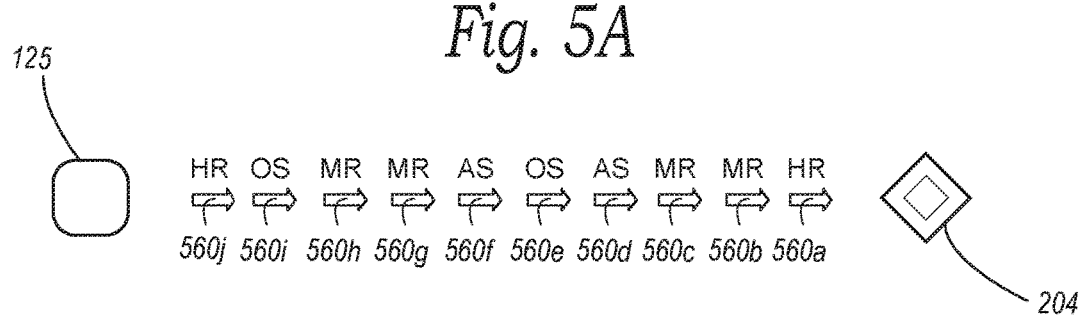
Fig. 5A
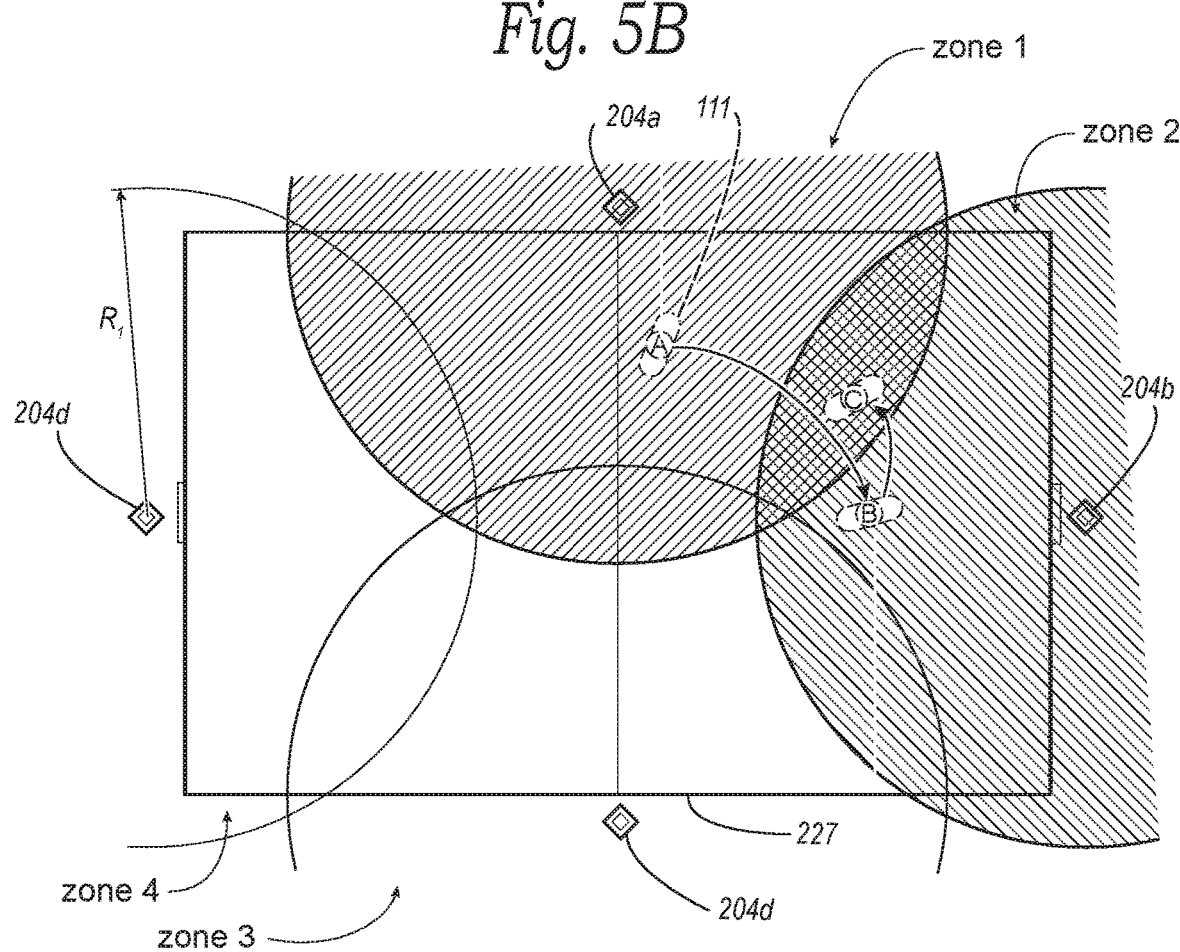
Fig. 5B
Fig. 5C

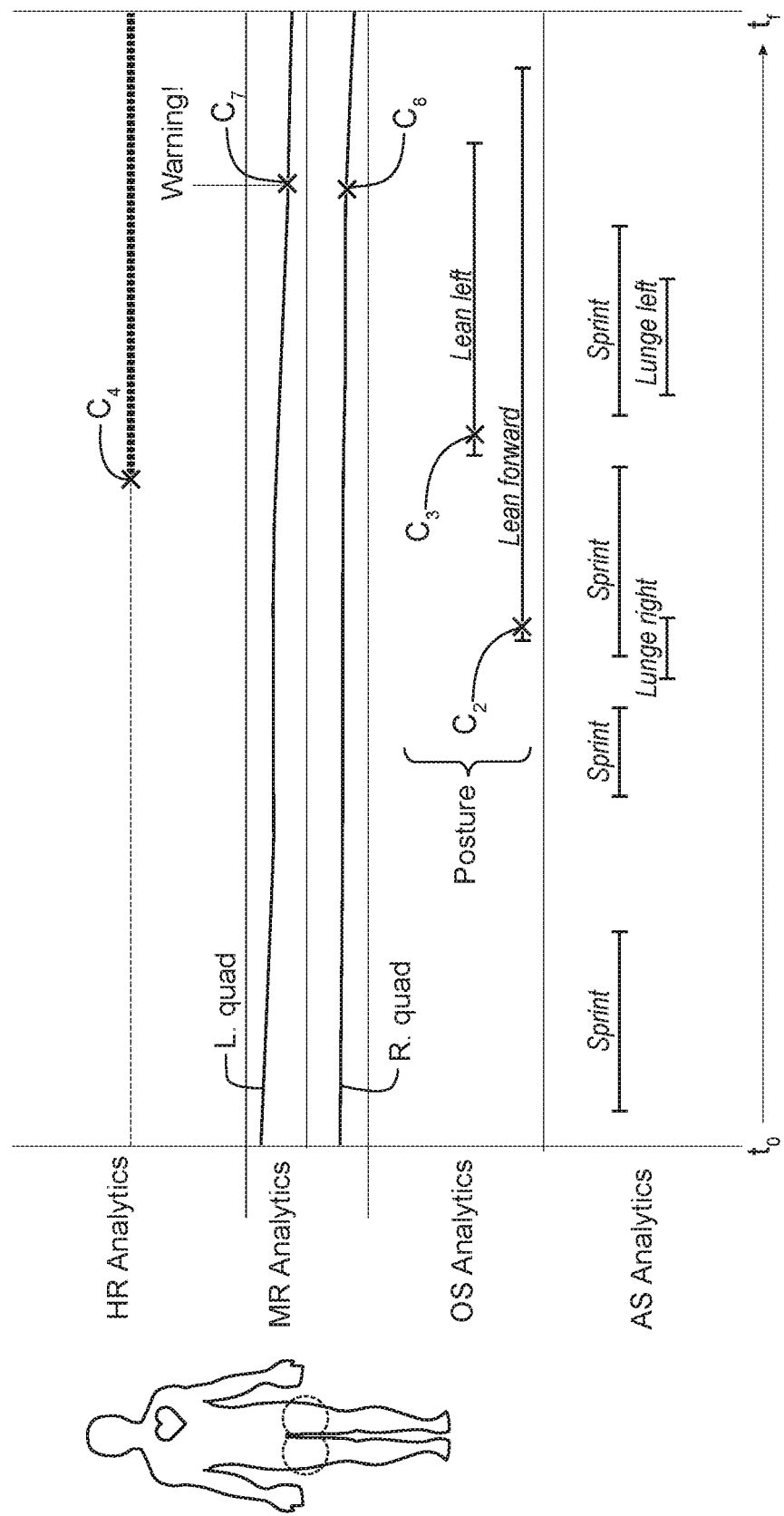

ALGORITHMS FOR DETECTING ATHLETIC FATIGUE, AND ASSOCIATED METHODS

BACKGROUND

Market research and subject matter experts are showing that fatigue can make an athlete more susceptible to injury, and may, in fact, be one of the leading causes of injuries. Thus, there is a need to detect the onset of fatigue while an athlete is actively training, conducting practice, or participating in a live game. When a trainer (e.g., an athletic trainer or coach) detects signs of fatigue, the trainer can intervene to reduce the likelihood of fatigue-related injury. For example, when a trainer detects fatigue, the trainer may instruct the athlete to slow down or focus on technique. In addition or alternately, a trainer may pull the athlete from a game or a practice session for rest and recovery.

One of the challenges with detecting fatigue is that traditional methods of monitoring athletic performance, such as real-time heart rate monitoring, do not in and of themselves necessarily indicate when an athlete is fatigued. For example, an athlete experiencing lack of sleep, may still exhibit a normal or expected heart during a practice session, but may experience earlier on-set of fatigue due to lack of sleep. As a result, the athlete may have a heightened susceptibility to fatigue-induced injury that the trainer may be unaware of because the athlete's heart rate appeared to be normal. Accordingly, there remains a need for cost effective systems and methods that can detect early onset of fatigue which may not be readily detectable by real-time monitoring alone.

BRIEF DESCRIPTION OF THE DRAWINGS

The foregoing aspects and many of the attendant advantages of this invention will become more readily appreciated with reference to the following detailed description, when taken in conjunction with the accompanying drawings, wherein:

FIGS. 4A-4E are diagrams showing a controller and other components of a performance monitor in accordance with embodiments of the presently disclosed technology.

FIG. 5A is a diagram illustrating a sample data packet in accordance with an embodiment of the presently disclosed technology.

FIG. 5B is a diagram showing a data packet in a stream of notification packets in accordance with an embodiment of the presently disclosed technology.

FIG. 5C is diagram showing gateways and wireless detection zones in accordance with another embodiment of the presently disclosed technology.

FIGS. 10A-10D are diagrams representing scenarios for detecting fatigue via analytics in accordance with another embodiment of the presently disclosed technology.

DETAILED DESCRIPTION

A. System Overview

An analytics system that enables coaches and athletic trainers to determine when an athlete is experiencing fatigue, such as during a practice session or a live game. In general, the onset of fatigue can be based on a variety of factors, such as local muscular fatigue, neural fatigue, and environmental fatigue. For example, local muscular fatigue can be caused by insufficient energy to power high intensity workouts, neural fatigue can occur when performance is largely inhibited by neural rather than muscular factors, and environmental fatigue can be caused by lack of sleep, stress, jetlag, etc.

Analytics systems configured in accordance with various embodiments of the present technology, however, can address these and other limitations of traditional methods of detecting fatigue and/or monitoring athletic performance. As described below, the system can provide analytics that are predictive in nature and can detect the early onset of fatigue which may not be readily detectable by real-time monitoring alone. This, in turn, provides the opportunity for earlier intervention and corrective action to reduce the risk of fatigue-related injuries.

Figure 1A:
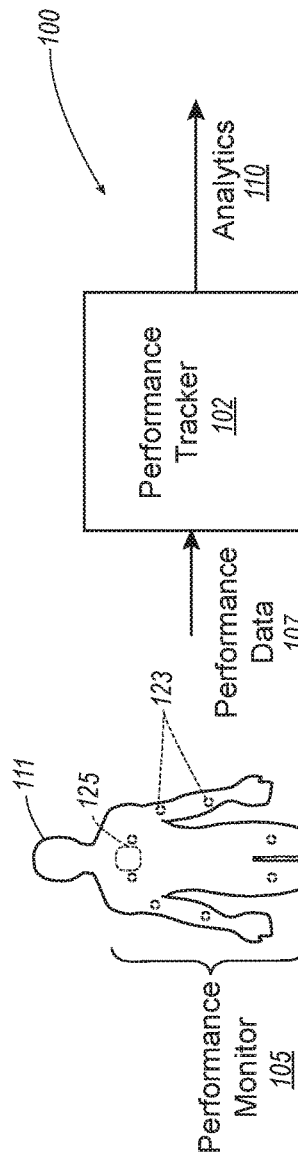
FIG. 1A is a diagram illustrating an analytics system configured in accordance with an embodiment of the present technology.

FIG. 1A is a diagram illustrating an analytics system 100 ("system 100") configured in accordance with an embodiment of the present technology. The system 100 includes a performance tracker sub-system 102 ("performance tracker 102") and a performance monitoring sub-system 105 ("performance monitor 105") worn by a user, such as an athlete 111. The performance monitor 105 includes an on-board controller 125 ("controller 125") and sensors 123 that can be integrated into the athlete's clothing (not shown), such as the athlete's shirt, pants, etc. The athlete's clothing and the integrated controller 125 and sensors 123 can be collectively referred to as "a wearable." In operation, the controller 125 is configured to produce real-time or near real-time data ("real-time data") 107 during a live session S1 (FIG. 1B), such as during a live game, a practice session, or conditioning.

Figure 1B:
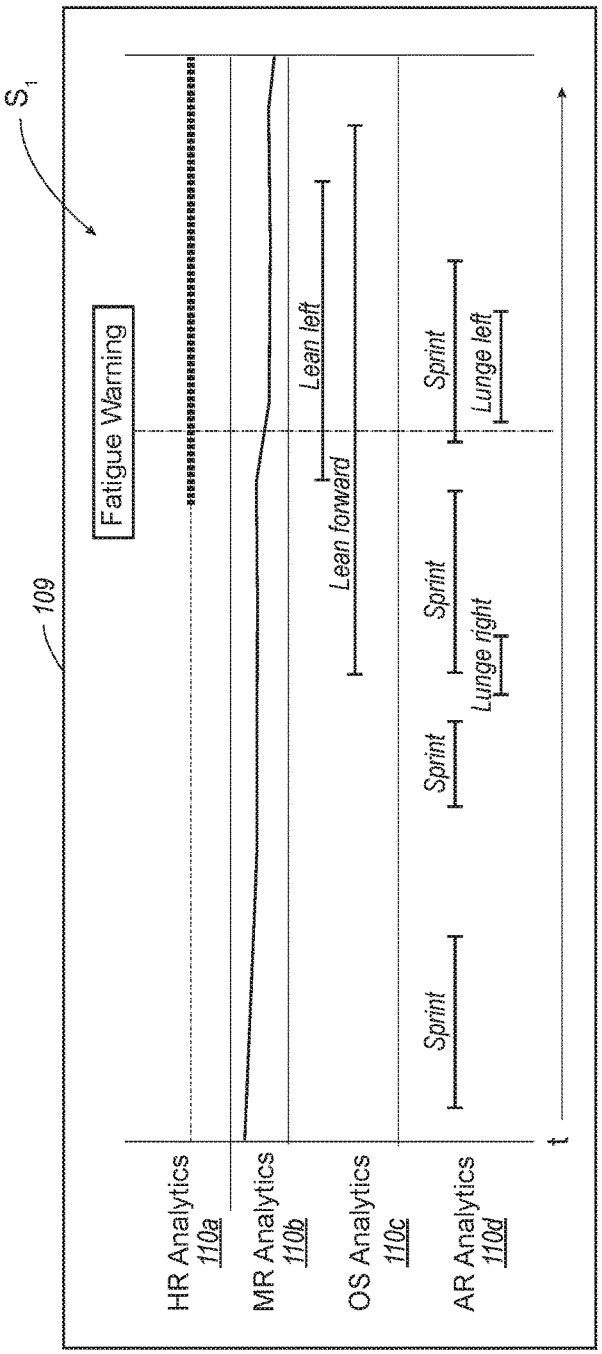
FIG. 1B is a diagram illustrating a graphical user interface configured in accordance with an embodiment of the presently disclosed technology.

FIG. 1B is a diagram illustrating a graphical user interface 109 presenting visual feedback corresponding to analytics 110 produced by the performance tracker 102 (FIG. 1A) during the live session S1. The interface 109 can be presented, for example, by an App running on a trainer's mobile computing device (not shown). In the illustrated example, the analytics 110 include heart rate (HR) analytics 110a, muscle response (MR) analytics 110b, orientation state (OS) analytics 110c, and activity state (AS) analytics 110d. The analytics 110 are produced over an evaluation period of a certain duration (e.g., 1 hour, 30 minutes, 15 minutes, 5 minutes, etc.). The analytics 110 are based on (1) on the real-time data 107 received during the live session S1 and (2) other analytics produced during previous live sessions, which can include analytics from tens, hundreds, or thousands of previous sessions. As described below, the system 100 can use the analytics 110 to produce preemptive indications, warnings, and alarms that alert the trainer when an athlete is fatigued or may soon encounter fatigue.

Figure 2:
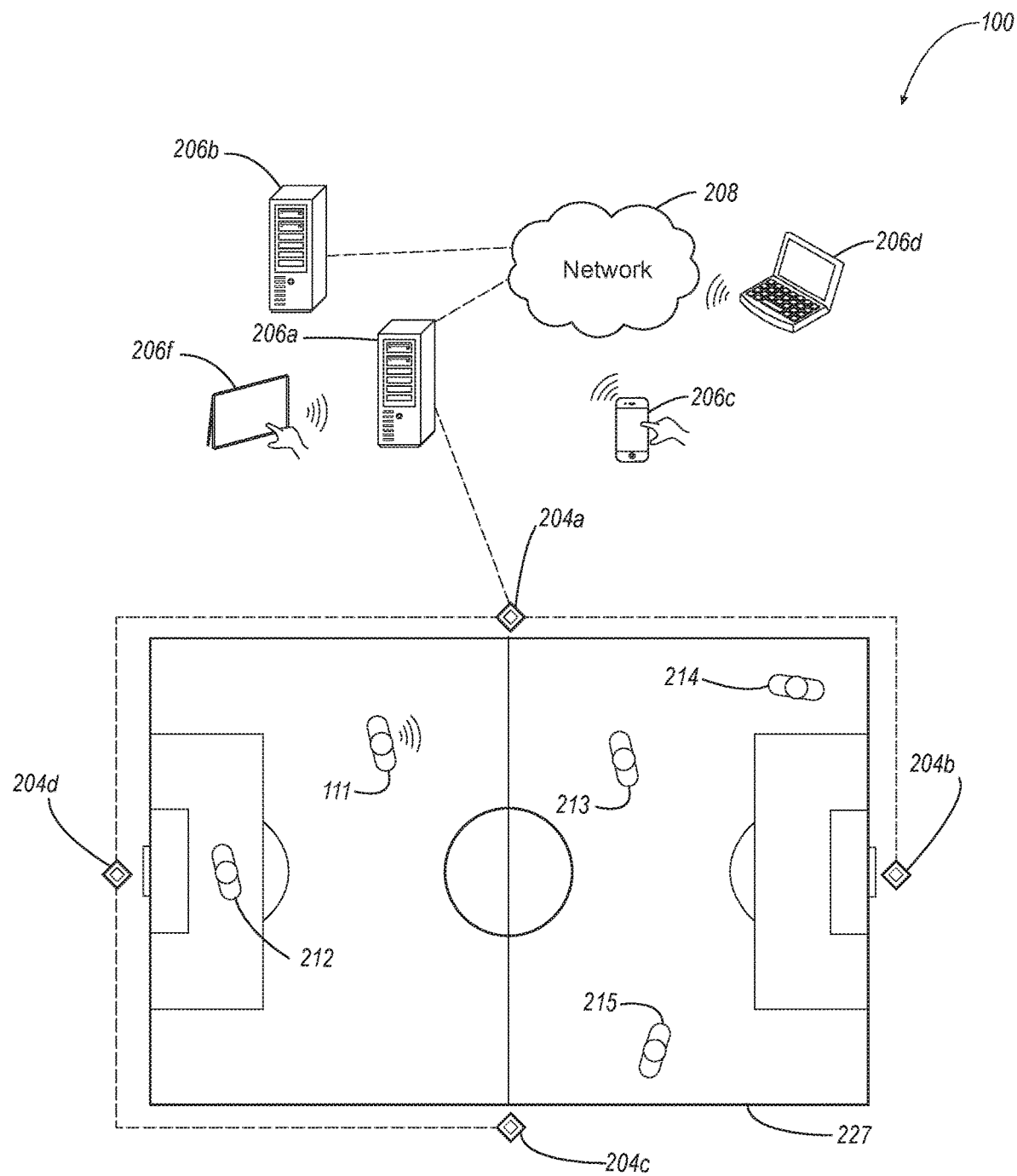
FIG. 2 is a diagram illustrating components of a system in accordance with an embodiment of the presently disclosed technology.

FIG. 2 is a diagram illustrating components of the system 100 in further detail. The performance monitor 105 (FIG. 1A) is configured to communicate with one or more computing devices 206 via a plurality of gateway devices 204 positioned along a periphery of a monitoring region 227, such as a soccer-field, an athletic arena, etc. The computing devices 206 are connected to one another via a network 208. The computing devices 206 are configured to receive, view, evaluate, store, and/or otherwise interact with data associated with the analytics 110 (FIG. 1B). For example, intermediary or back-end server devices 206a and 206b can exchange and process communications over the network 208, store a central copy of data, globally update content, etc. Examples of well-known computing devices, systems, environments, and/or configurations that may be suitable for use with the technology include, but are not limited to, personal computers, server computers, handheld or laptop devices, cellular telephones, tablet devices, multiprocessor systems, microprocessor-based systems, set-top boxes, programmable consumer electronics, network PCs, minicomputers, mainframe computers, databases, distributed computing environments that include any of the above systems or devices, or the like.

One or more of the computing devices 206 can be configured to individually or collectively carry out the functions of the performance tracker 102 (FIG. 1A) for producing the analytics 110. In various embodiments, the various computing devices 206 can process real-time data produced by other athletes 212-215 that are monitored in the monitoring region 227 of the gateways 204. As described below, the gateways 204 are configured to forward the real-time data 107 (FIG. 1A) to the upstream computing devices 206 for processing.

B. Computing Devices

Figure 3:
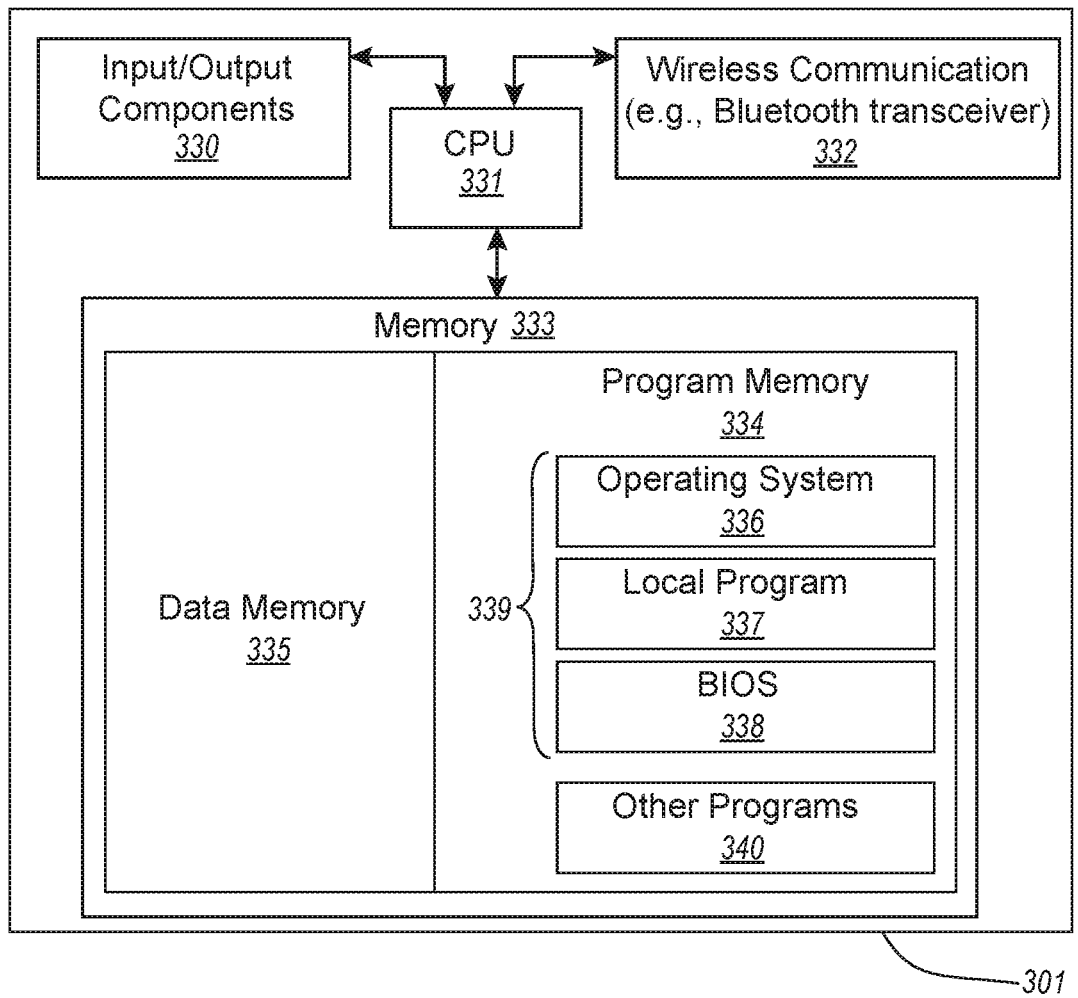
FIG. 3 is block diagram illustrating components of a system in accordance with an embodiment of the presently disclosed technology.

FIG. 3 is block diagram illustrating components that can be incorporated into a computing device 301, such as one of the computing devices 206 (FIG. 2), the gateways 204 (FIG. 2), and the performance monitor 105 (FIG. 1A). The computing device 301 includes input and output components 330. Input components can be configured to provide input to a processor such as CPU 331, notifying it of actions. The actions are typically mediated by a hardware controller that communicates according to one or more communication protocols. The input components 330 can include, for example, a mouse, a keyboard, a touchscreen, an infrared sensor, a touchpad, a pointer device, a camera- or image-based input device, a pointer, and/or a microphone.

The CPU 331 can be a single processing unit or multiple processing units in a device or distributed across multiple devices. The CPU 331 can be coupled to other hardware components via, e.g., a bus, such as a PCI bus or SCSI bus. Other hardware components can include communication components 333, such as a wireless transceiver (e.g., a WiFi or Bluetooth transceiver) and/or a network card. Such communication components 332 can enable communication over wired or wireless (e.g., point-to point) connections with other devices. A network card can enable the computing device 301 to communicate over the network 208 (FIG. 2) using, e.g., TCP/IP protocols. Additional hardware components may include other input/output components, including a display, a video card, audio card, USB, firewire, or other external components or devices, such as a camera, printer, CD-ROM drive, DVD drive, disk drive, Blu-Ray device, and/or speakers.

The CPU 331 can have access to a memory 333. The memory 333 includes volatile and non-volatile components which may be writable or read-only. For example, the memory can comprise CPU registers, random access memory (RAM), read-only memory (ROM), and writable non-volatile memory, such as flash memory, hard drives, floppy disks, CDs, DVDs, magnetic storage devices, tape drives, device buffers, and so forth. The memory 333 stores programs and software in programming memory 334 and associated data (e.g., configuration data, settings, user options or preferences, etc.) in data memory 335. The programming memory 334 contains an operating system 336, local programs 337, and a basic input output system (BIOS) 338, all of which can be referred to collectively as general software 339. The operating system can include, for example, Microsoft Windows™, Apple iOS, Apple OS X, Linux, Android, and the like. The programming memory 334 also contains other programs and software 340 configured to perform various operations. The various programs and software can be configured to process the real-time data 107 of the athlete 111 (FIG. 1A) and produce corresponding analytics, such as during the live session S1 (FIG. 1B), as described in greater detail below. Those skilled in the art will appreciate that the components illustrated in the diagrams described above, and in each of the diagrams discussed below, may be altered in a variety of ways.

C. Performance Monitor

FIGS. 4A-4C are diagrams showing the controller 125 and other components of the performance monitor 105 (FIG. 1) in further detail. Referring to FIG. 4A, the controller 125 can include certain hardware and software components similar to those described above with reference to FIG. 3. For example, the controller 125 can include a CPU 431, memory 433, and a wireless transmitter 432 (e.g., Bluetooth transmitter) over which the controller 125 communicates with the gateway devices 204 (FIG. 2). In some embodiments, the controller 125 can be packaged in a water-resistant, resilient housing 442 having a small form factor.

Referring to FIG. 4B, the controller 125 can be embedded within the athlete's clothing, such as a shirt 445a and pants 445b (collectively "clothing 445"). In other embodiments, the controller 125 can be inserted into a pocket 443 in the user's clothing and/or attached using Velcro, snap, snap-fit buttons, zippers, etc. In some embodiments, the controller 125 can be removable from the clothing 445, such as for charging the controller 125. In other embodiments, the controller 125 can be permanently installed in the athlete's clothing 445.

Referring to FIGS. 4A-4E together, the controller 125 is operably coupled to electrocardiogram (ECG) sensors 423a, electromyography (EMG) sensors 423b, an orientation sensor 423c (FIG. 4A; e.g., a gyroscope), and an acceleration sensor 423d (FIG. 4A; e.g., an accelerometer) that are carried at various locations on the athlete's clothing 445. The sensors 423 can be connected to the controller 125 using thin, resilient flexible wires (not shown) and/or conductive thread (not shown) woven into the clothing 445. The gauge of the wire or thread can be selected to optimize signal integrity and/or reduce electrical impedance.

The ECG and EMG sensors 423a and 423b can include dry-surface electrodes distributed throughout the athlete's clothing 445 and positioned to make necessary skin contact beneath the clothing along predetermined locations of the body. In some embodiments, the sensors can include an optical detector, such an optical sensor for measuring heart rate. The fit of the clothing can be selected to be sufficiently tight to provide continuous skin contact with the individual sensors 423a and 423b, allowing for accurate readings, while still maintaining a high-level of comfort, comparable to that of traditional compression fit shirts, pants, and similar clothing. In various embodiments, the clothing 445 can be made from compressive fit materials, such as polyester and other materials (ex. Elastaine) for increased comfort and functionality. In some embodiments, the controller 125 and the sensors 423 can have sufficient durability and water-resistance so that they can be washed with the clothing 445 in a washing machine without causing damage. In these and other embodiments, the presence of the controller 125 and/or the sensors 423 within the clothing 445 may be virtually unnoticeable to the athlete. In one aspect of the technology, the sensors 423 can be positioned on the athlete's body without the use of tight and awkward fitting sensor bands. In general, traditional sensor bands are typically uncomfortable for an athlete, and athletes can be reluctant to wear them.

The ECG sensors 423a can include RA, LA, and RL (floating ground) sensors positioned on the athlete's chest and/or waist. In some embodiments, the ECG sensors 423a can be placed on the athlete's inner thighs, and/or upper quads. The EMG sensors 423b can be positioned adjacent to targeted muscle groups, such as the large muscle groups of the pectoralis major, rectus abdominis, quadriceps femoris, biceps, triceps, deltoids, gastrocnemius, hamstring, and latissimus dorsi. The EMG sensors 423b can also be coupled to floating ground near the athlete's waist or hip.

The orientation and accelerations sensors 423c and 423d can be disposed at a central position 449 located between the athlete's shoulders and upper back region. In some embodiments, the central, upper back region can be an optimal location for placement of the orientation and acceleration sensors 423c and 423d because of the relatively small amount of muscle tissue in this region of the body, which prevents muscle movement from interfering with the accuracy of the orientation and acceleration readings. In other embodiments, the orientation sensor 423c and/or the acceleration sensor 423d can be positioned centrally on the user's chest, tail-bone, or other suitable locations of the body. In various embodiments, the orientation and acceleration sensors 423c and 423d can be positioned adjacent the controller 125, or integrated into the same packaging 422 as controller 125, as shown in FIG. 4A. In other embodiments, the orientation sensor 423c and/or the acceleration sensor 423d can be positioned at other locations. For example, the orientation sensor 423c and/or the acceleration sensor 423d can be positioned on a waist band of the athlete's pants. In use, the acceleration and orientation sensors 423a and 423b can detect 3D orientation and 3D acceleration of the central position 449 (corresponding, e.g., to a center of mass or general movement). FIGS. 4E and 4F show the athlete in a lean left and lean forward orientation, respectively, that can be detected by the orientation sensor 423c and determined relative to the central location 449. In some embodiments, the lean left orientation can indicate whether the athlete 111 is limping or favoring one side or portion of the body than the other. The lean forward orientation can be indicative of a poor posture of the athlete beginning at the onset of fatigue, as described below. As further shown in FIGS. 4E and 4F, acceleration vectors Ax, Ay, and Az can be produced by the acceleration sensor 423d in response to movement of the athlete 111. In various embodiments, the acceleration vectors can be indicative of whether the athlete 111 is lunging to the left or right, accelerating in the forward or rearward directions, jumping or diving in the up and down directions, and/or performing various combinations of these motions or other motion(s).

In one aspect of this embodiment, the use of a single orientation sensor and a single acceleration sensor can reduce computational complexity of the various analytics 110 (FIG. 1B) produced by the system 100 (FIG. 1A). In particular, a reduced set of orientation and acceleration data may be sufficient for detecting various indicators of fatigue and other performance characteristics in conjunction with the other real-time data 107 (FIG. 1A) collected from the other sensors 423 and based on other analytics derived in previous live sessions, as described below. In other embodiments, however, the performance monitor 105 can include multiple acceleration sensors and/or orientation sensors, such as for detecting acceleration and/or orientation of one or more of the athlete's limbs.

Referring back to FIG. 4A, the controller 125 and the sensors 423 can be powered by a power device 448, such as a rechargeable battery carried within the controller's housing 422. In some embodiments, the power device 448 can be a kinetic energy device (having, e.g., piezoelectrics) configured to convert and store energy generated by the athlete 111 (FIG. 1A) while wearing the clothing 445 and/or while the clothing 445 is being cleaned in a washing machine and/or a dryer.

In some embodiments, the performance monitor 105 (FIG. 1A) does not include the pants 445b and/or includes sensors positioned in other articles of clothing in addition to or in lieu of the pants 445b, such as shorts, a headband, socks, shoes, etc. In some embodiments, the performance monitor 105 can include other input and/or output components 443, such as a feedback device (e.g., a speaker or a vibration generator) that provides real-time feedback to the athlete while wearing the clothing. For example, the feedback can include a series of audible beeps and/or vibrations that increase in frequency as the athlete is approaching a state of fatigue detected by the performance tracker 102 (FIG. 1A), as described below. In these and other embodiments, the controller 125 can be configured to directly communicate with a Bluetooth headset for voice communication with the trainer, to download real-time data stored in the memory 433 after completion of a live session (e.g., for further analysis), and/or to perform other functions. In some embodiments, the performance monitor 105 can include a magnetometer for self-calibration of the orientation sensor 423c and/or the accelerometer 423d. A magnetometer may also be used in conjunction with or in lieu of the orientation sensor for providing orientation data.

In additional or alternate embodiments, the performance monitor 105 (FIG. 1A) can include a separate controller 446 worn on the athlete's pants 445b. The separate controller 446 can be similar to the controller 125 worn on the athlete's shirt 445a, and is connected to the individual sensors 423 located on the pants 445b. The separate controller 446 can be configured to communicate with the controller 125 and/or with the gateways 204 (FIG. 2) independent of the controller 125.

D. Controller Communication

In operation, the controller 125 of the performance monitor 105 (FIG. 1A) is configured to process and packetize the data it receives from the sensors 423. The controller 125 broadcasts the packetized data for detection by the gateway devices 204, which, in turn, forward the data to the performance tracker 105 (FIG. 1A) to produce analytics.

FIG. 5A is a diagram illustrating an example packet 560a, which can be referred to as a notification packet, which is produced and broadcast by the controller 125 to the gateways 204, and FIG. 5B is a diagram showing the packet 560a in a stream of notification packets 560 sent from the controller 125 to an individual gateway device 204. In the illustrated embodiment, the packet 560a is formatted according to a Bluetooth low energy protocol, known to those skilled in the art as Bluetooth LE, BLE, or Bluetooth Smart protocol. Referring to FIG. 5A, the packet 560 can include a packet identifier 561, a payload portion 563, and characteristics 562 corresponding to the payload 563. The payload 563 of the packet contains the real-time data 107 (FIG. 1A) produced by the various sensors 423 (FIGS. 4A-4C). In the case of Bluetooth LE, the controller 125 can broadcast packets in which the real-time data 107 has been sampled at periodic intervals with a sample period Ps having a duration on the order of 10 s of milliseconds (12.5 ms intervals). In one aspect of this embodiment, the packet 560 can be assigned a characteristic corresponding to the type of real-time data contained in the payload 563 (e.g., heart rate, muscle response, orientation, and acceleration characteristics).

Referring to FIG. 5B, the packet 560a and the other notification packets 560b-f can be broadcasted from the controller 125 acting as a server to which the gateway 204 (FIG. 2) subscribes. For example, the notification packets 560 can be sent to the gateway 204 once they have received an initial advertisement packet (including the initial subscription information describing the payload, characteristics, and other information to be sent via the notification messages) and exchanged initial confirmation and acknowledgement messages. In one aspect of the technology, the controller 125 does not require confirmation of receipt of the broadcasted packets, which reduces signal latency between the controller 125 and the gateway 204. In other embodiments, the controller 125 can communicate with the gateways 204 using other wireless protocols, including non-native protocols (e.g., Z-wave), or wireless protocols having faster transmission speeds than Bluetooth LE. In some embodiments, the controller 125 can be a client that connects to the gateway(s) of its choosing, initiating data exchange.

In the illustrated example, the individual packets 560 can be sent synchronously (e.g., at a frequency in a range of, e.g., 2-60 packets per second (e.g., 30 packets per second). Some types of packets can be sent more frequently than others. For example, packets containing acceleration data and/or muscle response data in the payload may be sent more frequently than packets containing orientation data. Packets containing orientation data in the payload can be sent more frequently that packets containing heart rate data. In other embodiments, the packets can be sent asynchronously and/or at different frequencies than shown in the illustrated examples.

E. Gateways

FIG. 5C is a diagram showing the gateways 204 and wireless detection zones associated with the corresponding gateways 204. Each of the gateways 204 can include hardware components similar to the hardware components of the computing device 301 described above with reference to FIG. 3. For example, the gateways 204 can include a CPU, memory, and a wireless transceiver over which the gateways communicate with one or more of the upstream computing devices 206, such as via the WiFi protocol. The zones of the gateways can have a cover range defined by a radius R1, and can each extends over at least a portion of the monitoring region 227. In various embodiments, the gateways can be discrete, battery-powered units that have a non-obtrusive form factor. In these and other embodiments, the gateways can be strategically positioned around a facility, a playfield, or other area where an athlete's performance is to be monitored.

In operation, the gateways 204 receive and forward the packets broadcasted by the performance monitor associated with the athlete 111. For example, when the athlete is at position A in FIG. 5C, the first gateway 204a will detect and forward the packets associated with the athlete 111, but will not detect packets when the athlete 111 is located at position B because this is out of that gateway's zone. At position B, the second gateway 204b will detect and forward the packets because the athlete 111 is in the second gateway's zone. In some cases, the athlete 111 may be in two overlapping zones, such as when the athlete is at position C shown in FIG. 5C. In such instances, both the first and second gateways 204a and 204b will receive the same broadcasted packets, and both gateways will forward these packets to the performance tracker 102 (FIG. 1A). In one aspect of the technology, the performance tracker 102 can disregard a duplicative packet. For example, the performance tracker 102 can disregard a packet it receives from the second gateway 204b when it has already received the same packet from the first gateway 204a (or vice versa). In some embodiments, the process tracker 102 and/or the gateways 204 can save all packets, including duplicate packets, for subsequent processing. In various embodiments the gateways can cache data locally, such as if an internet connection is lost and/or for subsequent download.

In another aspect of the technology, the gateways 204 do not detect the actual location of the athlete 111. Additionally, the real-time data and analytics are not calculated based on physical coordinates, such as geospatial coordinates. As such, the gateways 204 can be positioned and moved around before and during a live session without little or no effect on the performance data and analytics produced by the system 100 (i.e., so long as the gateways provide suitable zone coverage the monitoring region 227). In a related aspect, the gateways 204 do not require permanent installation and can be readily transported and set-up in different environments, which limits infrastructure costs for installing the system. Further, the gateways 204 can operate in indoor environments (e.g., covered stadiums and indoor practice areas) in which GPS signals are difficult to detect. Additionally, the analytics are not restricted to the limited resolution and computational intensive processing needed by traditional systems that typically require computation of acceleration, motion, etc., based on the athlete's spatial coordinates at a particular point in time. Instead, each of the packets 530 contains real-time data that can be processed without calculating the athlete's actual location in real-time due to the types of real-time data collected and the nature in which the analytics are derived, as described below.

Further, additional and/or redundant gateways can be added to the monitoring region 227 to ensure that there is sufficient zone coverage and/or to accommodate a larger numbers of users. For example, in some embodiments, the monitoring region 227 can be covered by 6, 8, 12, 20, or more gateways having corresponding zones. In some embodiments, the individual gateways can accommodate a maximum number of athletes at a given time (e.g., 6 athletes). In such embodiments, two or more gateways can be positioned in the vicinity of one another to increase the maximum number of athletes that can be detected in a given zone. In still further embodiments, a gateway can be assigned to a single athlete and/or a gateway can have a zone that covers an entire monitoring region 227. In some embodiments, a single gateway can be assigned to an athlete (e.g., a goalie) that typically remains in the same general location within the monitoring region 227.

Figure 6A:
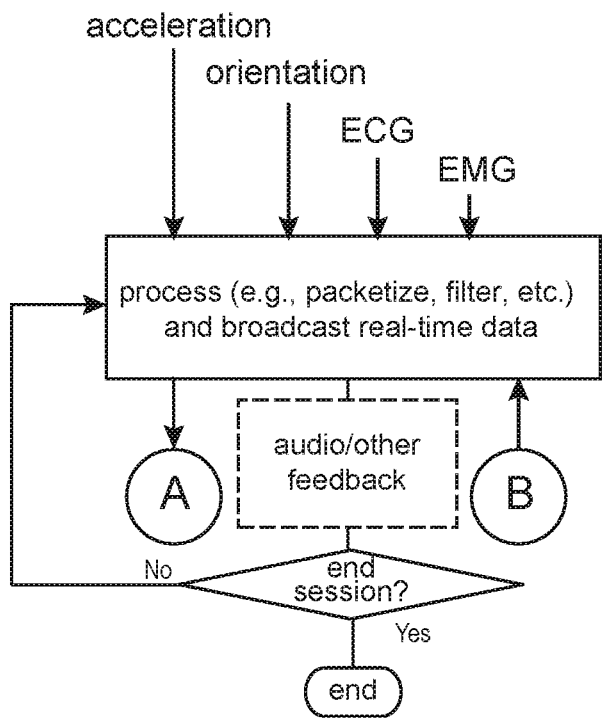
FIG. 6A shows a flow diagram of an example process that can be carried out by a performance monitor in accordance with another embodiment of the presently disclosed technology.
Figure 6B:
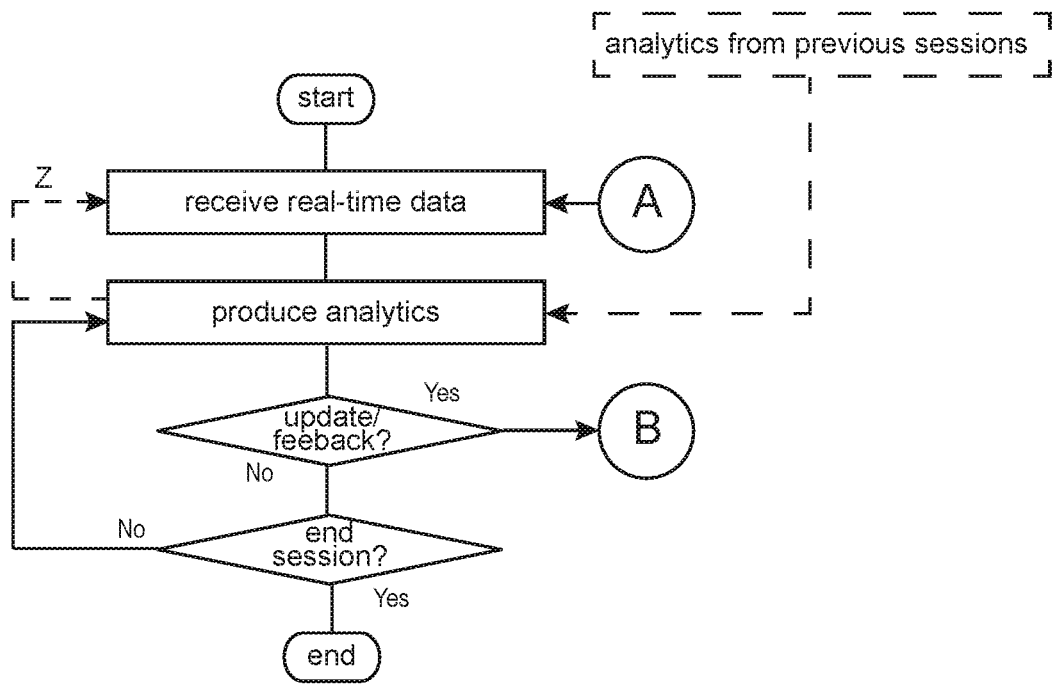
FIG. 6B shows a flow diagram of an example process that can be carried out by a performance tracker in accordance with another embodiment of the presently disclosed technology.

FIG. 6A shows a flow diagram of an example process that can be carried out by the performance monitor 105 (FIG. 1A). FIG. 6B shows a flow diagram of an example process that can be carried out by the performance tracker 102 (FIG. 1A). As discussed above, and as shown by the arrow Z in FIG. 6B, the performance tracker 102 can manage the flow of data sent from multiple zones and during zone changes.

F. HR Analytics

Figure 7A:
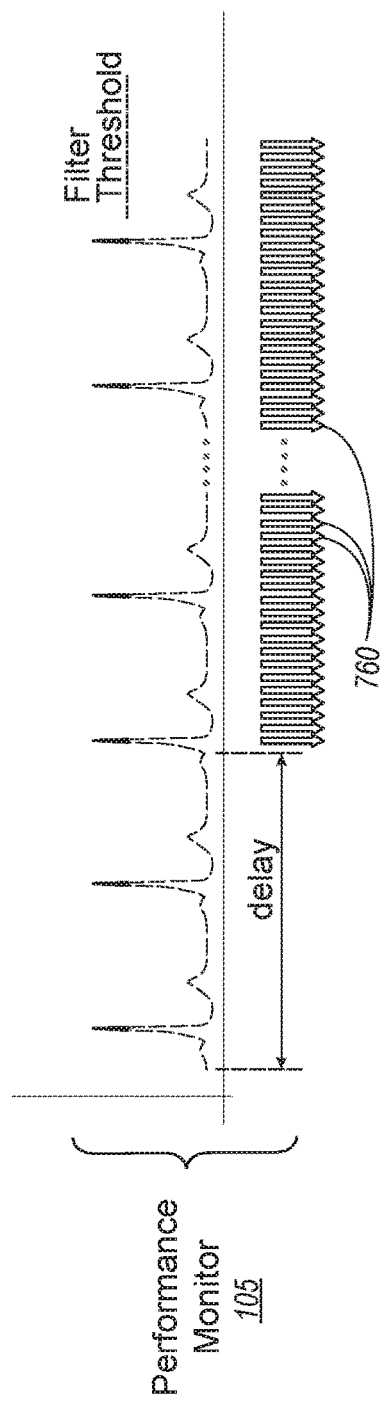
FIG. 7A is a diagram representing data received from electrocardiogram (ECG) sensors of a performance monitor in accordance with another embodiment of the presently disclosed technology.
Figure 7B:
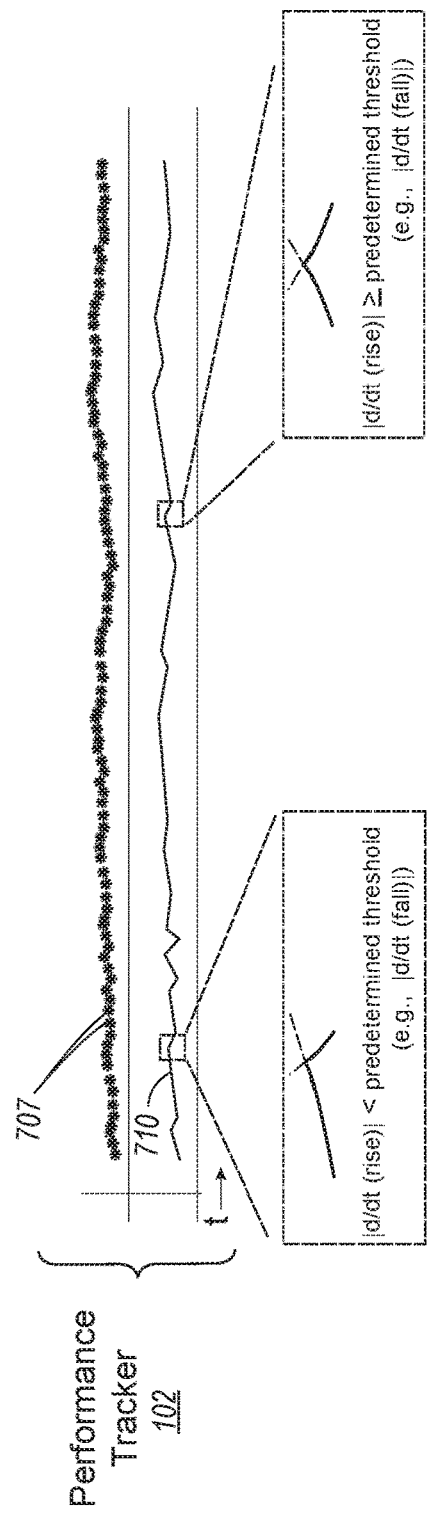
FIG. 7B is a diagram showing a heart rate (HR) analytics in accordance with another embodiment of the presently disclosed technology.

FIG. 7A is a diagram representing data (e.g., an analog signal) received from the ECG sensors of the performance monitor 105, and FIG. 7B is a diagram showing corresponding HR analytics 710 produced by the performance tracker 102. Referring first to FIG. 7A, the performance monitor 105 processes analog ECG signals received from the ECG sensors 423a (FIGS. 4B and 4C). In the illustrated example, the performance monitor 105 filters out amplitudes of the ECG signal that fall below a threshold, and measures intervals between the pulse peaks to provide real-time or near real-time data 707 ("real time data 707") in the form of a series of beat-per-minute (BPM) samples (FIG. 7B) in the payload of packets 760 sent to the performance tracker 102. In some embodiments, other ECG data can be collected, in addition to or in lieu of BPM.

In some embodiments, ECG can be monitored using a single lead measurement between left-arm (LA), right-arm (RA) and grounding (RL—right-leg). Filtering can be done using a bandpass filter from 1 Hz to 150 Hz, including a notch filter for the elimination of 60 Hz signal. In addition, the system can use a high common mode rejection ratio with the gain of about 100 for higher (150 Hz) frequencies. The hardware of the controller 125 (FIG. 1A) can include a common amplification circuit for ECG and EMG. The grounding can also be common, allowing for similar reference points. Standardizing on common ground can drive simplification of circuitry requiring different op-amp gain, while maintaining similar signal integrity filtering.

In various embodiments, the processing of the analog ECG signal and the other data signals described below (e.g., the raw EMG, orientation, and acceleration signals) can be slightly delayed (e.g., 1 to 3 second delay) before broadcasting the corresponding packets to the performance tracker 102. Such delay can be due to pre-processing of the raw data signals at the performance monitor 105 before broadcast. In some embodiments, pre-processing (e.g. filtering) can reduce the amount of data sent between the performance monitor 105 and the tracker 102, which can further increase downstream processing efficiency of the analytics, and the delay can have negligible or no impact on the resultant analytics.

Referring to FIG. 7B, the performance tracker 102 process the packets 760 and produces the HR analytics 710 based on the corresponding real-time data 707 received over a live session (e.g., the live session S1 (FIG. 1B)). In one aspect of this embodiment, the performance tracker 102 detects the rate of change in falling and rising heart rates over the live session, and determines when the latter is greater than the former. Without being bound by theory, it is believed that a key indicator of fatigue occurs when the rate of rising heart rate exceeds a predetermined threshold. Also, without being bound by theory, it is believed that such threshold can be based on the rate of change in falling heart rate as the athlete's heart rate returns to a resting rate.

G. MR analytics

Figure 8A:
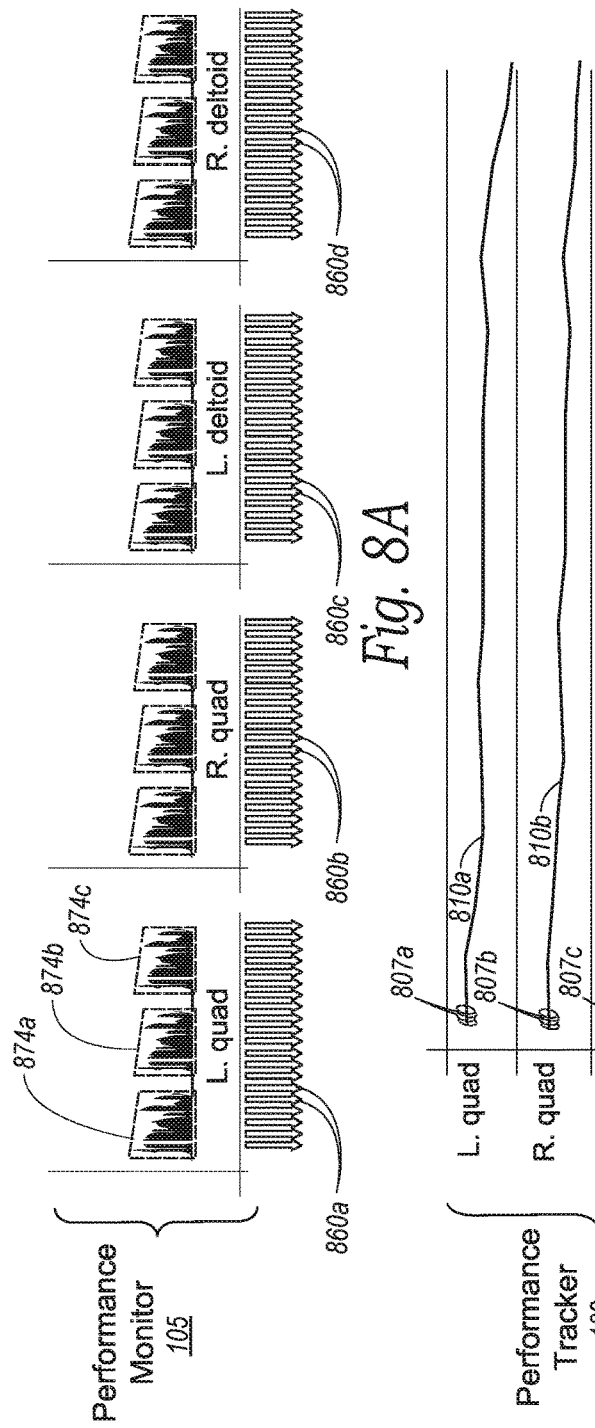
FIG. 8A is a diagram representing data received from electromyography (EMG) sensors of a performance monitor in accordance with another embodiment of the presently disclosed technology.
Figure 8B:
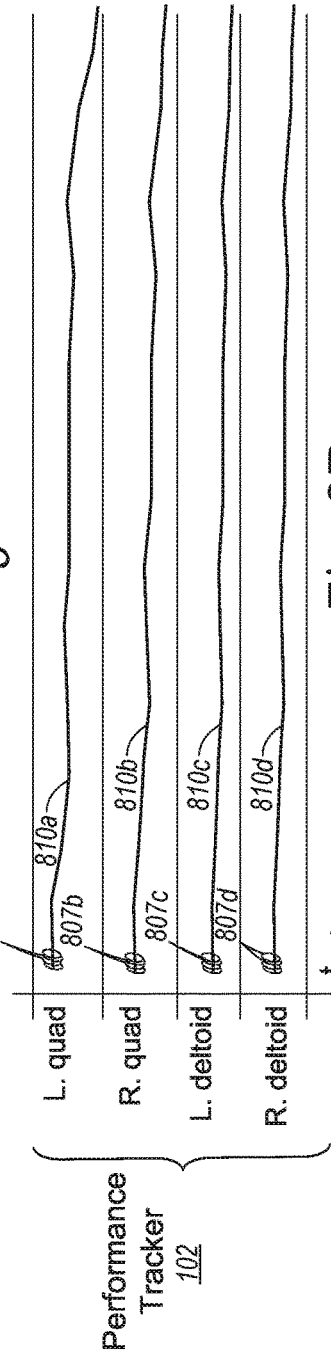
FIGS. 8B and 8C are diagrams showing muscle response (MR) analytics produced by a performance tracker in accordance with another embodiment of the presently disclosed technology.

FIG. 8A is a diagram representing data (e.g., an analog signal) received from the EMG sensors of the performance monitor 105, and FIG. 8B is a diagram showing corresponding MR analytics 810 produced by the performance tracker 102. Referring first to FIG. 8A, the performance monitor 105 processes EMG signals received from the EMG sensors 423b (FIGS. 4B and 4C). In the illustrated example, the EMG can have magnitudes that correspond to muscle responses of the various muscles groups monitored by the EMG sensors, such as the quadriceps and the deltoids, as shown in FIG. 8A. The magnitudes of the sampled EMG signals can be provided in the payload of packets 860a-d sent to the performance tracker 102 and corresponding to real time or near real-time date 807 ("real time data 807"; FIG. 8B) of a particular muscle group that is to monitored. While only the EMG signals from the quadriceps and deltoids are shown in the illustrated example, EMG data associated with other muscle groups can be sent to and processed by the performance tracker 102, such as data associated with the pectoralis major, rectus abdominis, biceps, triceps, gastrocnemius, hamstring, latissimus dorsi, etc.

In some embodiments, EMG can be monitored using multiple electrodes for different muscle groups, as discussed above. In certain embodiments, only large muscles are monitored to simplify processing. In such embodiments, total body performance can be tracked based on scaling of large muscle readings. The controller 125 can be configured to pre-filter EMG signals from, e.g., 80 Hz through, e.g., 400 Hz. By starting from 80 Hz, the system may not need additional notch filtering to bypass 60 Hz noise frequency. In some embodiment, processing can be based on recursive low-pass filtering, as follows:

$$y[n]=1/2(x[n]+y[n-1])$$

The system can be configured to binarize muscle output through ADC conversion and allow for easy comparison of absolute mV output. In addition, any missed data bits, which can be created by disconnect of electrodes from muscles, can be mitigated by applying the integrated moving averages, as follows:

$$(1-B)^d = \sum_{k=0}^{\infty} \binom{d}{k}(-B)^k$$

Figure 8C:
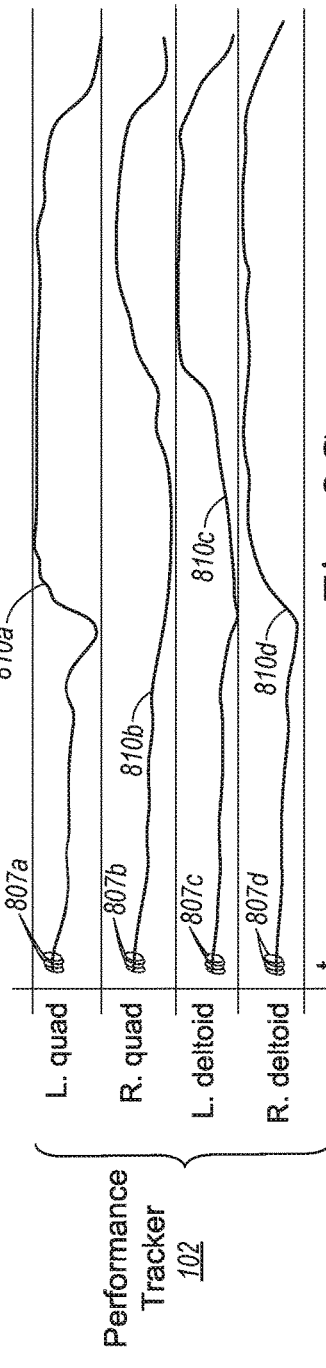

Referring to FIG. 8B, the performance tracker 102 process the packets 860 and produces the AS analytics 810 based on the corresponding real-time data 807 received over a live session (e.g., the live session S1 (FIG. 1B)). In one aspect of this embodiment, the performance tracker 102 detects the running averages of the EMG pulses to detect changes in muscles response over time, such as decreasing muscle response magnitude FIG. 8B) and increasing muscle recovery time (FIG. 8C showing increased muscle response recovery time 801b for R. quad and 810c for L. deltoid. In some embodiments, running averages 874 (FIG. 1A) can be calculated on-board by the controller 125 (FIG. 1A) to reduce bandwidth.

H. OS and AS Analytics

Figure 9A:
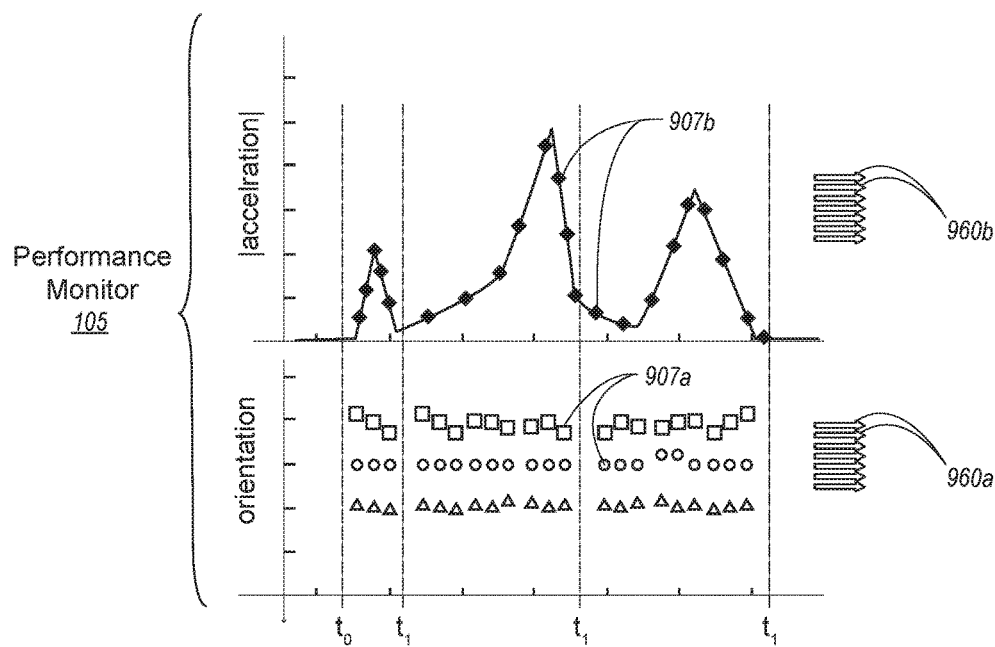
FIG. 9A is a diagram representing data received from orientation and acceleration sensors in accordance with another embodiment of the presently disclosed technology.
Figure 9B:
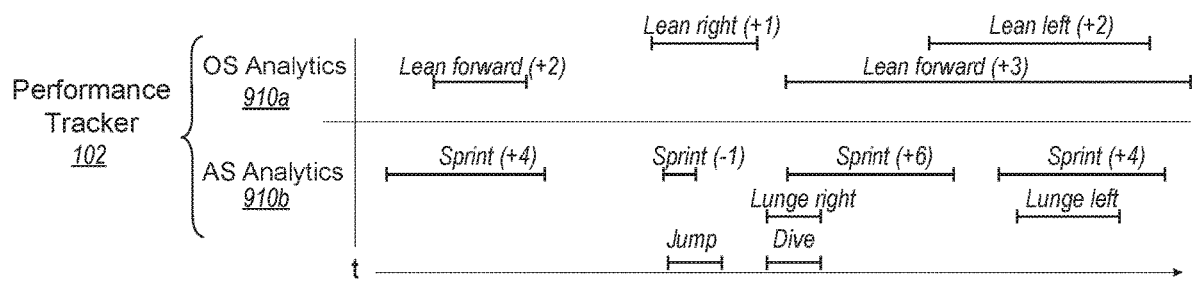
FIG. 9B is a diagram showing orientation (OR) and acceleration (AS) analytics in accordance with another embodiment of the presently disclosed technology.
Figure 10A:
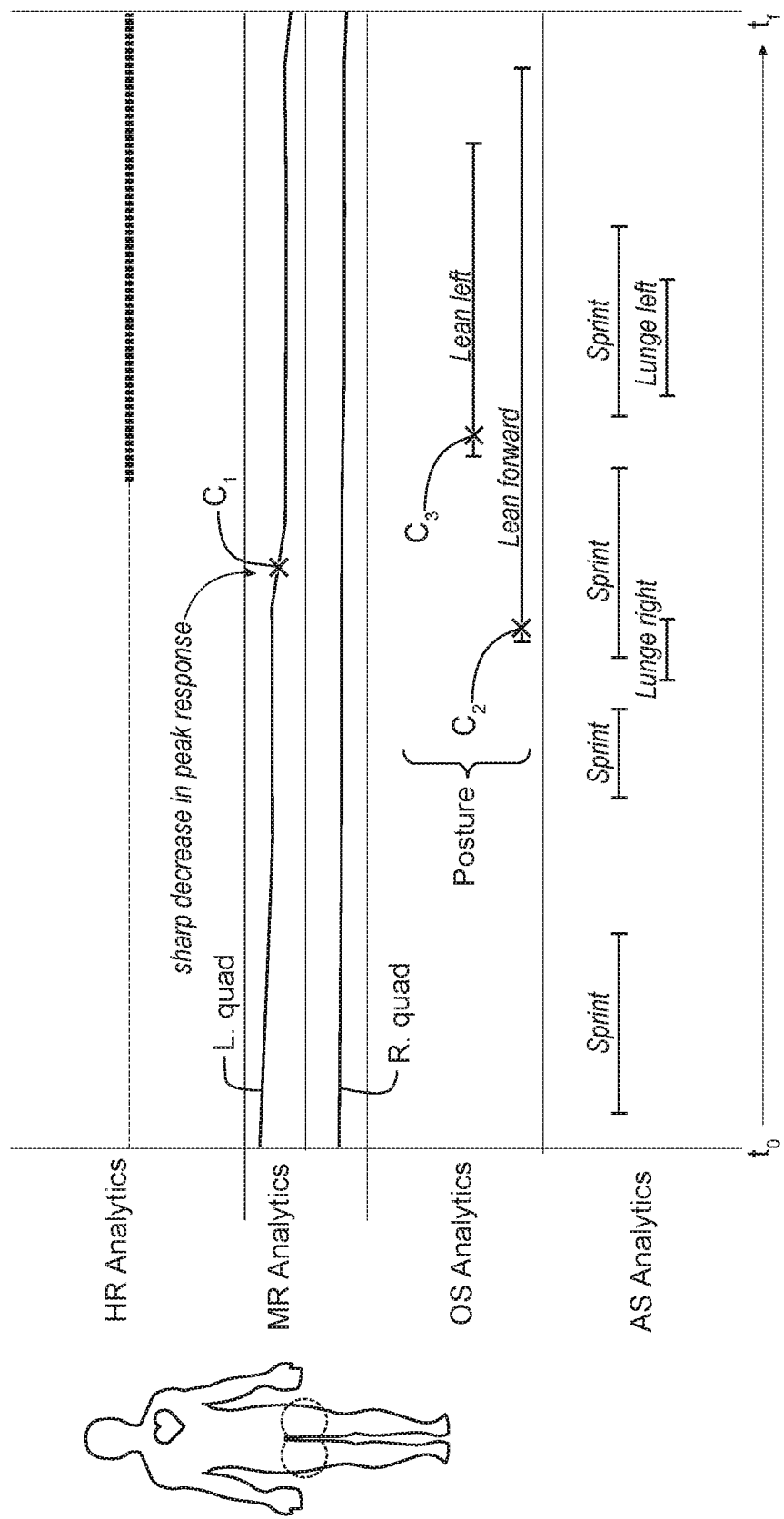
Figure 10B:
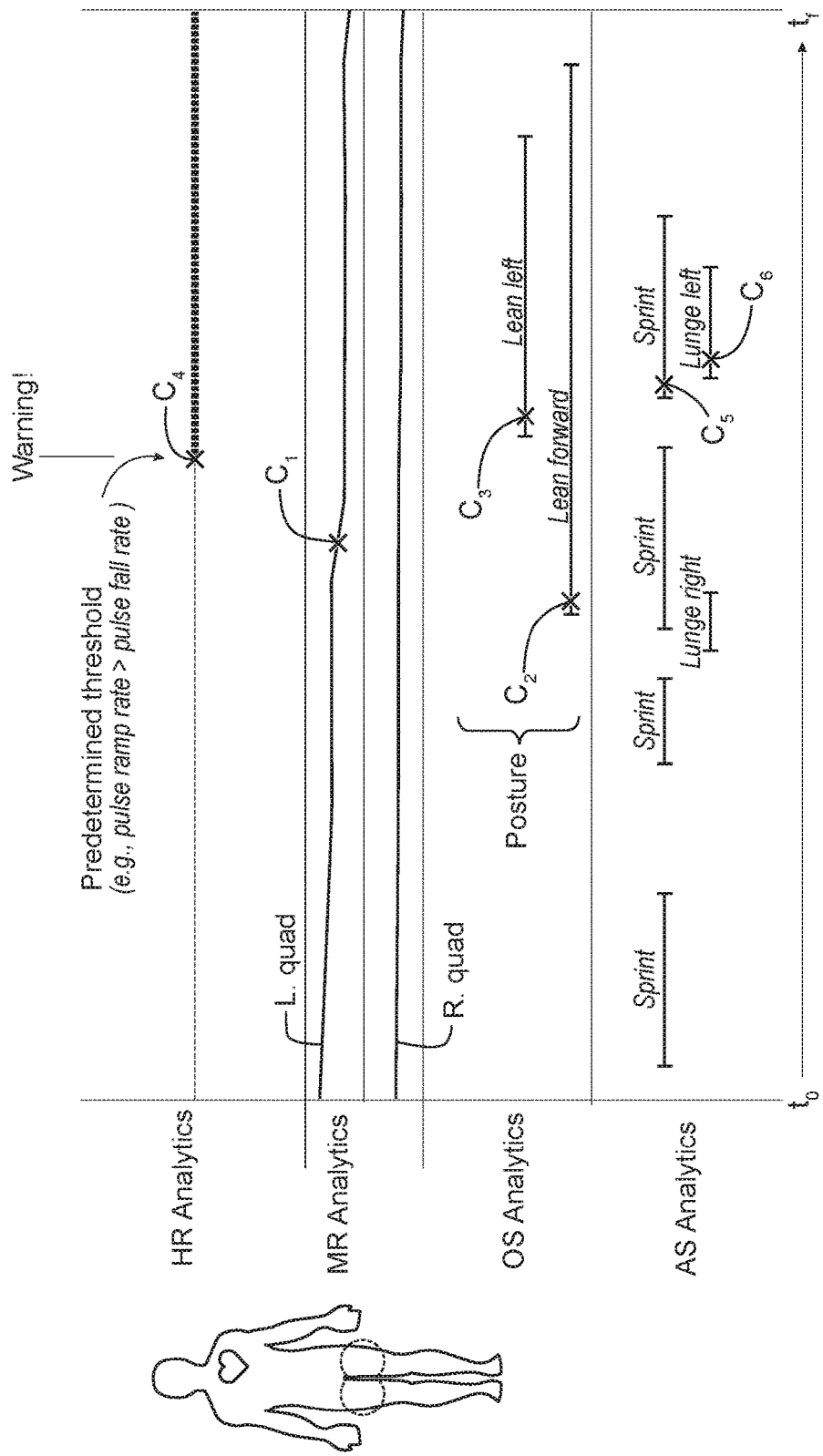
Figure 10C:
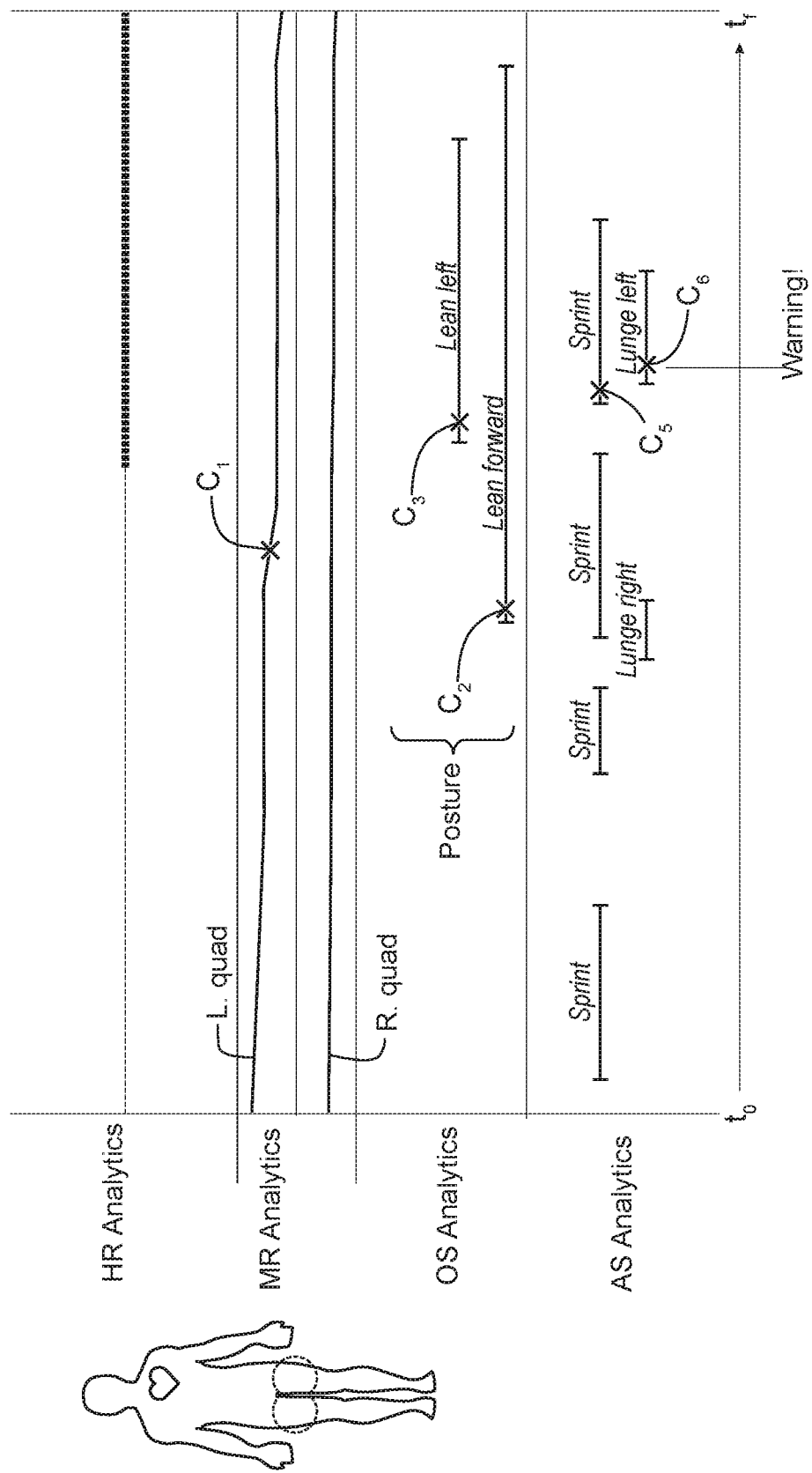

FIG. 9A is a diagram representing data received from the orientation and acceleration sensors of the performance monitor 105, and FIG. 9B is a diagram showing corresponding OR and AS analytics 910a and 910b, respectively, produced by the performance tracker 102. Referring to FIG. 9A, real-time or near real time orientation data ("real-time data 907a") and real-time or near real-time acceleration data ("real-time data 907b") can be sent to the performance tracker 102 via corresponding packets 960a and 960b, respectively. In some embodiments, the real-time data 907 can be discrete data points.

Referring to FIG. 9B, the performance tracker 102 can use the real-time acceleration and orientation data to detect the relative orientation (e.g., posture) of the user and acceleration associated with various types of motion, such as leaning, sprinting, diving, jumping, stopping, repetitive motion, etc. In some embodiments, the analytics can include an indicator of magnitude that represents the extent to which the athlete is exerting a particular type of motion. For example, a sprint motion with a magnitude of "6" can indicate that the athlete is accelerating at a faster rate than when the magnitude is "4," while a negative value (−) can indicate that the user is slowing down. Similarly, a magnitude assigned to an orientation can indicate that the extent to which the user is leaning, slouching, etc., in a particular direction.

I. Fatigue Detection Scenarios

FIGS. 10A-10D are diagrams representing scenarios for detecting fatigue via analytics generated during a live session. Tables 1A-1B, below, describes parameters associated with these scenarios. In general, the analytics can include various algorithms that allow trainers to predict what will happen with an athlete's performance, in addition to receive real-time data. Further, the more the athlete uses the system 100 (FIG. 1A), the more responsive it will become, allowing for more accurate performance forecast. For example, the system 100 can employ machine learning and/or other artificial intelligence to detect patterns and trends in the athlete's heart response, muscle responses, orientation(s), acceleration(s), explosiveness (i.e., combination of acceleration and muscle response), etc. In some embodiments, the system can employ cloud learning that enables the athlete, trainer, and other users to evaluate performance and compare performance to other athletes, including anonymous athletes. As described in the various examples below and in the drawings, the analytics can be correlated and compared to draw insights, conclusions, and warnings.

TABLE 1A

| | | Warning generated? |
|---|---|---|
| MR analytics | $C_1$ = sharp decrease in peak muscle response of left quad | No |
| OS analytics | $C_2$ and $C_3$ = lean forward and lean left posture | Possible when $C_1$, $C_2$, and $C_3$ have been detected |

Note:
Condition $C_1$ might be detected due to a previous injury (e.g., a left ACL injury) for which the athlete has gone through rehabilitation. $C_2$ and $C_3$ can be indicative of a posture that the athlete assumes when the previous injury is implicated. The posture and EMG association may be determined based on analytics from previous sessions.

TABLE 1B

| | | Warning generated? |
|---|---|---|
| MR analytics | $C_1$ = sharp decrease in peak muscle response of left quad | No |
| OS analytics | $C_2$ and $C_3$ = lean forward and lean left posture | Possible when $C_1$, $C_2$, and $C_3$ have been detected |
| HR analytics | $C_4$ = predetermined threshold reached | Yes, when $C_1$, $C_2$, $C_3$, and $C_4$ have been detected |

Note:
Risk of injury and onset of fatigue may be detected when condition $C_4$ is subsequently detected. The ECG and EMG association and/or the ECG and posture association may be determined based on analytics from previous sessions.

TABLE 1C

| | | Warning generated? |
|---|---|---|
| MR analytics | $C_1$ = sharp decrease in peak muscle response of left quad | No |
| OS analytics | $C_2$ and $C_3$ = lean forward and lean left posture | Possible when $C_1$, $C_2$, and $C_3$ have been detected |
| AS analytics | $C_5$ and $C_6$ = lunge left and sprinting activity | Yes, when $C_1$, $C_2$, $C_3$, $C_5$, and $C_6$ have been detected |

Note:
Risk of injury and onset of fatigue may be detected when high levels of activity implicate stress on the left leg. The EMG and acceleration association and/or the posture and acceleration association may be determined based on analytics from previous sessions.

TABLE 1D

| | | Warning generated? |
|---|---|---|
| MR analytics | $C_7$ and $C_8$ = decreasing muscle response in legs | No |
| OS analytics | $C_2$ and $C_3$ = lean forward and lean left posture | Possible when $C_2$, $C_3$, $C_7$, and $C_8$ have been detected |
| HR analytics | $C_4$ = predetermined threshold reached | Yes, when $C_2$, $C_3$, $C_4$, $C_7$, and $C_8$ have been detected |

Note:
Risk of injury and onset of fatigue may be detected when condition $C_4$ is subsequently detected. The EMG, posture, and ECG associations may be determined based on analytics from previous sessions.

J. Fatigue Detection Scenarios

Several sample use scenarios are outlined below. These sample use scenarios use the following terminology:
"Aaron"—Athlete
"Carl"—Coach
"Terry"—Trainer
"Danny"—Doctor Scenario 1: Aaron is performing a bench press while Carl and Terry are located further away, without visuals on Aaron's posture. The system will track Aaron's movement and muscle/heart performance, and provide any alarms (custom set) to Carl and Terry. This data then will be connected (if injury happens) which then Danny can use to understand what is the target for a successful recovery.

Scenario 2: Aaron is running a lot while increasingly moving laterally. With detected fatigue, both Terry and Danny can notice that the muscle output is becoming lower, while the body movement is becoming more unbalanced, especially when moving laterally. Both Terry and Danny can notify Carl to remove Aaron from the game/practice or tell him to slow down, preventing possible ACL/MCL injuries.

Scenario 3: Aaron is performing explosive exercises (e.g., exercises that combine acceleration and muscle output). While Aaron might think that he is doing his best, Terry and Danny can see that the muscle output is not continuous but rather keeps varying between 50% and 70%, while the ECG is varying between 110 and 130 bpm. Here, Terry can drive Aaron to go stronger, maximizing his performance, knowing that Aaron actually has capacity to push harder.

Data flow for the above scenarios:
 All of the data is collected and uploaded to a server. There, coaches can view data and analyze it in real-time. However, Aaron and other players also have an option to log in and understand their performance against other anonymous players.
 Carl, Terry, and Danny can share the data and analyze it in real time against custom alarms that they set before deploying the system.

Examples of tracked events:
 Performance Maximization
 Fatigue
 Movement tracking
 Muscle activation
 Cardiovascular system load study
 Musculoskeletal motion tracking While various advantages associated with some embodiments of the disclosure have been described above, in the claims, and the Appendix in the context of those embodiments, other embodiments may also exhibit such advantages, and not all embodiments need necessarily exhibit such advantages to fall within the scope of the invention. For example, while various embodiments are described in the context of an athlete (e.g., a professional or collegiate athlete), in some embodiments users of the system can include novice or intermediate users, such as users, trainers, and coaches associated with a high school sports team, an athletic center, a professional gym, etc. Accordingly, the disclosure can encompass other embodiments not expressly shown or described herein.

The embodiments of the invention in which an exclusive property or privilege is claimed are defined as follows:

1. A method for detecting a fatigue of an athlete by monitoring real-time athletic performance of the athlete by a performance tracker operationally coupled to a display, wherein the performance tracker is configured to execute the method comprising:
 monitoring a heart rate (HR) of the athlete by a wearable electrocardiogram (ECG) sensor carried by the athlete;
 monitoring a magnitude of a muscle response (MR) of the athlete by wearable electromyography (EMG) sensors carried by the athlete, wherein the EMG sensors are positioned adjacent to a plurality of target muscle groups;
 transferring the HR and the MR of the athlete from a controller to at least one remote gateway as real-time or near real-time data packets that include both the HR and MR of the athlete, wherein the controller is attached to the athlete;
 determining a rate of change of the HR over a first period of time while the athlete is engaged in a given exercise;
 determining a rate of change of the MR over a second period of time while the athlete is engaged in the given exercise, wherein the first period and the second period are directly linked and correspond to repetitive instances of the given exercise;
 comparing the rate of change of the HR to a first predetermined threshold;
 comparing the rate of change of the MR to a second predetermined threshold;
 determining whether the athlete is fatigued based on comparing the rate of change of the HR to the first predetermined threshold and comparing the rate of change of the MR to the second predetermined threshold for the given exercise; and
 displaying a fatigue warning on the display.

2. The method of claim 1, wherein the rate of change of the HR is positive over the first period of time, and wherein the rate of change of the HR is greater than the first predetermined threshold, the method further comprising:
 determining that the athlete is fatigued.

3. The method of claim 1, wherein the rate of change of the HR is negative over the first period of time, and wherein the rate of change of the HR is lower than the first predetermined threshold, the method further comprising:
 determining that the athlete is fatigued.

4. The method of claim 1, further comprising:
 monitoring an orientation state (OS) of the athlete by a wearable orientation sensor carried by the athlete; and
 determining whether the athlete is fatigued at least in part based on an output of the wearable orientation sensor.

5. The method of claim 4, wherein the wearable orientation sensor is a gyroscope.

6. The method of claim 1, further comprising:
 monitoring an activity state (AS) of the athlete by a wearable activity sensor carried by the athlete; and
 determining whether the athlete is fatigued at least in part based on an output of the wearable activity sensor.

7. The method of claim 6, wherein the wearable activity sensor is an accelerometer.

8. The method of claim 1, wherein the ECG sensor and the EMG sensors are washable.

9. The method of claim 1, further comprising:
 comparing a ramp rate of the HR to a fall rate of the HR during the first period of time, wherein the first period of time corresponds to the given exercise; and
 if the ramp rate of the HR is greater than the fall rate of the HR, determining that the athlete is fatigued.

10. The method of claim 1, further comprising:
 monitoring an orientation state (OS) of the athlete by a wearable orientation sensor carried by the athlete, wherein the orientation state indicates a posture or a relative orientation of the athlete; and
 determining whether the athlete is fatigued based on combined outputs of the wearable orientation sensor, the ECG sensor, and the EMG sensors.

11. The method of claim 1, further comprising:
 detecting running averages of the muscle response (MR) of the athlete during the second period of time; and
 determining whether the athlete is fatigued based on satisfying conditions of:
 a decreasing muscle response magnitude of the athlete within the running averages of the muscle response (MR) of the athlete going below a third predetermined threshold, and an increasing muscle recovery time of the athlete within the running averages of the muscle response (MR) of the athlete going above a fourth predetermined threshold.

12. A system for detecting a fatigue of an athlete by monitoring real-time athletic performance of the athlete, the system comprising:
- a performance monitor, comprising:
  - athlete's clothing comprising one or more articles of clothing,
  - a wearable electrocardiogram (ECG) sensor attached with the athlete's clothing, the ECG being configured for monitoring a heart rate (HR) of the athlete,
  - a plurality of wearable electromyography (EMG) sensors attached with the athlete's clothing adjacent to a plurality of target muscle groups, wherein the EMG sensors are configured for monitoring a magnitude of a muscle response (MR) of the target muscle groups of the athlete; and
  - a wearable controller attached with the athlete's clothing, the controller being configured to produce real-time or near real-time data based at least in part on input from the ECG sensor and the EMG sensors; and
- a performance tracker operationally coupled to a display, the performance tracker configured to:
  - receive data from the performance monitor,
  - determine a rate of change of the HR over a first period of time while the athlete is engaged in a given exercise;
  - determine a rate of change of the MR over a second period of time while the athlete is engaged in the given exercise, wherein the first period and the second period are directly linked and correspond to repetitive instances of the given exercise;
  - compare the rate of change of the HR to a first predetermined threshold;
  - compare the rate of change of the MR to a second predetermined threshold;
  - determine whether the athlete is fatigued based on comparing the rate of change of the HR to the first predetermined threshold and comparing the rate of change of the MR to the second predetermined threshold for the given exercise; and
  - display a fatigue warning on a-the display.

13. The system of claim 12, wherein the controller includes a wireless transceiver configured to communicate with the performance tracker.

14. The system of claim 12, further comprising:
an orientation sensor attached with the athlete's clothing, wherein the orientation sensor is configured to communicate with the controller.

15. The system of claim 14, wherein the orientation sensor is a gyroscope or a magnetometer.

16. The system of claim 12, further comprising:
an activity sensor attached with the athlete's clothing wherein the activity sensor is configured to communicate with the controller.

17. The system of claim 16, wherein the activity sensor is an accelerometer.

18. The system of claim 12, wherein the ECG sensor is washable.

19. The system of claim 12, wherein the athlete's clothing comprises a shirt and pants.

20. The system of claim 12, wherein the athlete's clothing comprises a conductive thread woven in the athlete's clothing.

* * * * *